(12) United States Patent
Heim et al.

(10) Patent No.: US 7,377,919 B2
(45) Date of Patent: May 27, 2008

(54) ELECTROSURGICAL INSTRUMENT

(75) Inventors: Warren P. Heim, Boulder, CO (US);
James L. Brassell, Boulder, CO (US);
Michael Olichney, Parker, CO (US)

(73) Assignee: Surginetics, Inc., Boulder, CO (US)

( * ) Notice: Subject to any disclaimer, the term of this patent is extended or adjusted under 35 U.S.C. 154(b) by 391 days.

(21) Appl. No.: 10/985,483

(22) Filed: Nov. 10, 2004

(65) Prior Publication Data
US 2005/0154385 A1    Jul. 14, 2005

Related U.S. Application Data

(60) Provisional application No. 60/518,708, filed on Nov. 10, 2003.

(51) Int. Cl.
*A61B 18/18*    (2006.01)
(52) U.S. Cl. .......................................... 606/45; 606/41
(58) Field of Classification Search ................ 606/41, 606/45–504
See application file for complete search history.

(56) References Cited

U.S. PATENT DOCUMENTS

| | | | |
|---|---|---|---|
| 874,178 | A | 12/1907 | De Forest |
| 1,713,970 | A | 5/1929 | Lowry et al. |
| 1,814,791 | A | 7/1931 | Ende |
| 3,799,168 | A | 3/1974 | Peters |
| 3,970,088 | A | 7/1976 | Morrison |
| 3,987,795 | A | 10/1976 | Morrison |
| 4,033,351 | A | 7/1977 | Hetzel |
| 4,043,342 | A | 8/1977 | Morrison, Jr. |
| 4,074,718 | A | 2/1978 | Morrison, Jr. |
| 4,161,950 | A | 7/1979 | Doss et al. |
| 4,202,337 | A | 5/1980 | Hren et al. |
| 4,228,800 | A | 10/1980 | Degler, Jr. et al. |
| 4,248,231 | A | 2/1981 | Herczog et al. |
| 4,314,559 | A | 2/1982 | Allen |
| 4,333,467 | A | 6/1982 | Domicone |

(Continued)

FOREIGN PATENT DOCUMENTS

WO    WO 94/28809    12/1994

(Continued)

OTHER PUBLICATIONS

PCT/US06/25123 International Search Report and Written Opinion.

(Continued)

*Primary Examiner*—Michael Peffley
(74) *Attorney, Agent, or Firm*—Hansen Huang Tech Law Group LLP

(57) ABSTRACT

An improved insulating layer for electrosurgical instruments and its use for electrosurgical instruments for reducing smoke generation at a surgical site is disclosed. The insulating layer may include a ceramic material that is substantially sealed with a coating comprising substantially of a material based on polydiorganosiloxanes or derivatives thereof that have been cured. Such an insulating layer may advantageously include one or more insulating materials with pores that have been sealed so as to prevent biological materials from entering the pores with such sealing material preferably containing one or more of silicate materials or materials that form silicates. Heat sinks may be included in various embodiments to establish a thermal gradient away from functional portions of the instrument.

46 Claims, 4 Drawing Sheets

U.S. PATENT DOCUMENTS

| | | | |
|---|---|---|---|
| 4,449,926 A | 5/1984 | Weiss | |
| 4,481,057 A | 11/1984 | Beard | |
| 4,492,231 A | 1/1985 | Auth | |
| 4,534,347 A | 8/1985 | Taylor | |
| 4,545,375 A | 10/1985 | Cline | |
| 4,565,200 A | 1/1986 | Cosman | |
| 4,589,411 A | 5/1986 | Friedman | |
| 4,622,966 A | 11/1986 | Beard | |
| 4,657,016 A | 4/1987 | Garito et al. | |
| 4,785,807 A | 11/1988 | Blanch | |
| 4,793,346 A | 12/1988 | Mindich | |
| 4,823,791 A | 4/1989 | D'Amelio et al. | |
| 4,848,337 A | 7/1989 | Shaw et al. | |
| 4,931,047 A | 6/1990 | Broadwin et al. | |
| 4,976,711 A | 12/1990 | Parins et al. | |
| 5,015,227 A | 5/1991 | Broadwin et al. | |
| 5,030,218 A | 7/1991 | Alexander | |
| 5,080,660 A | 1/1992 | Buelna | |
| 5,160,334 A | 11/1992 | Billings et al. | |
| 5,167,659 A | 12/1992 | Ohtomo et al. | |
| 5,267,994 A | 12/1993 | Gentelia et al. | |
| 5,308,311 A | 5/1994 | Eggers et al. | |
| 5,318,562 A | 6/1994 | Levy et al. | |
| 5,380,320 A * | 1/1995 | Morris | 606/33 |
| 5,382,247 A * | 1/1995 | Cimino et al. | 606/33 |
| 5,464,390 A | 11/1995 | Arnett et al. | |
| 5,520,684 A | 5/1996 | Imran | |
| 5,549,604 A | 8/1996 | Sutcu | |
| 5,554,172 A | 9/1996 | Horner et al. | |
| 5,562,659 A * | 10/1996 | Morris | 606/41 |
| 5,643,256 A | 7/1997 | Uruleta | |
| 5,693,050 A | 12/1997 | Speiser | |
| 5,697,926 A | 12/1997 | Weaver | |
| 5,702,387 A * | 12/1997 | Arts et al. | 606/45 |
| 5,713,895 A * | 2/1998 | Lontine et al. | 606/41 |
| 6,030,218 A | 2/2000 | Robinson | |
| 6,039,735 A | 3/2000 | Greep | |
| 6,059,783 A | 5/2000 | Kirwan, Jr. | |
| 6,066,137 A | 5/2000 | Greep | |
| 6,132,427 A | 10/2000 | Jones et al. | |
| 6,241,723 B1 | 6/2001 | Heim | |
| 6,533,781 B2 * | 3/2003 | Heim et al. | 606/45 |
| 6,685,704 B2 * | 2/2004 | Greep | 606/41 |
| 6,951,559 B1 * | 10/2005 | Greep | 606/41 |
| 2003/0109864 A1 | 6/2003 | Greep et al. | |
| 2003/0109865 A1 * | 6/2003 | Greep et al. | 606/41 |

FOREIGN PATENT DOCUMENTS

| | | |
|---|---|---|
| WO | WO 96/34571 | 11/1996 |
| WO | WO 97/11649 A | 4/1997 |
| WO | 9940858 A1 | 8/1999 |

OTHER PUBLICATIONS

PCT/US06/26122 International Search Report and Written Opinion.
PCT/US2005/025681 International Search Report with Written Opinion.
PCT/US2005/025681 International Preliminary Report on Patentability.
PCT/US06/26123 International Search Report and Written Opinion, Jan. 2007.
PCT/US06/26122 International Search Report and Written Opinion, Jan. 2007.
PCT/US2005/025681 International Search Report with Written Opinion, Jan. 2007.
PCT/US2005/025681 International Preliminary Report on Patentability, Mar. 2007.

* cited by examiner

ELECTROSURGICAL INSTRUMENT

CROSS-REFERENCE TO RELATED APPLICATIONS

This application claims priority to U.S. Provisional Patent Application Ser. No. 60/518,708, filed on Nov. 10, 2003, and entitled "ELECTROSURGICAL INSTRUMENT", the disclosure of which is incorporated herein by reference in its entirety.

FIELD OF THE INVENTION

The present invention relates to surgical methods and apparatus for applying an electrosurgical signal to a tissue site to achieve a predetermined surgical effect, and more particularly, to improved means and methods for insulating electrosurgical instruments to achieve a predetermined surgical effect with reduced attendant smoke generation at the surgical site.

BACKGROUND OF THE INVENTION

The potential applications and recognized advantages of employing electrical energy in surgical procedures continue to increase. In particular, for example, electrosurgical techniques are now being widely employed to provide significant localized surgical advantages in both open and laparoscopic applications, relative to traditional surgical approaches.

Electrosurgical techniques typically entail the use of a hand-held instrument, or pencil, that transfers radio frequency (RF) electrical energy to a tissue site, a source of radio frequency (RF) electrical energy, and an electrical return path device, commonly in the form of a return electrode pad positioned under a patient (i.e., a monopolar system configuration) or a smaller return electrode positionable in bodily contact at or immediately adjacent to the surgical site (i.e., a bipolar system configuration). The waveforms produced by the RF source yield a predetermined electrosurgical effect, namely tissue cutting or coagulation.

During transfer of RF electrical energy to a tissue site the parts of the instrument contacting or near the tissue become hot. Among the problems caused by such heating in proximity to tissue is the formation of a coating consisting of tissue and thermally decomposed tissue products, called eschar, that can adhere to the instrument and interfere with its proper function. Electrosurgical instruments have been proposed that are coated with materials in attempts to provide a surface from which eschar is more easily removed than from bare metal. For example, U.S. Pat. No. 4,785,807 describes a stainless steel blade coated with a form of polytetrafluoroethylene (PTFE), U.S. Pat. No. 5,702,387 describes metal blades coated with polysiloxane (specifically, polydiorganosiloxane) elastomer, and U.S. Pat. No. 6,511,479 describes metal blades coated with polysiloxanes. These coatings, and in particular, polysiloxane, coatings tend to be soft and can be removed from the blades with only modest scraping, e.g., by scraping with a thumbnail. The PTFE and the polysiloxane coatings have been found, with use, to recede from the regions closest to where energy discharge occurs leading to an increase in the amount of metal exposed and to lead to excessive heating of at least parts of the instruments, leading to eschar accumulations and smoke. Therefore, for certain applications, the need exists for more durable coatings for such surgical instruments.

Despite numerous advances in the field, currently-employed electrosurgical techniques often generate substantial smoke at the surgical site. Such smoke occurs as a result of tissue heating and the associated release of hot gases/vapor from the tissue site (e.g., in the form of an upward plume). As will be appreciated, any generation of smoke may impede observation of the surgical site during surgical procedures. Additionally, the generation of smoke results in attendant fouling of the atmosphere in the surgical theater. Clearly, these environmental impacts may adversely detract from the performance of medical personnel. Further, there is growing concern that the smoke may be a medium for the transport of pathogens away from the surgical site, including viruses such as HIV. Such concerns have contributed to the use of face shields and masks by surgical personnel.

To date, implemented approaches to deal with smoke have focused on the use of devices that either evacuate the smoke by sucking the same into a filtering system, or that merely blow the smoke away from the surgical site by a pressurized gas stream. Smoke evacuators typically require the movement of large amounts of air to be effective. As such, evacuators tend to be not only noisy but also space consuming. Approaches for blowing smoke away from the surgical site fail to address many of the above-noted concerns, since smoke is not actually removed from the surgical environment. Moreover, both of the above-noted approaches entail the use of added component, thereby increasing the cost and complexity of electrosurgical systems.

Recently, U.S. Pat. No. 6,287,305 has revealed that electrosurgical accessories, including blades, can substantially reduce smoke production by using a metal that has sufficiently high thermal conductivity and insulating the devices except for an exposed edge region where electrosurgical energy is transferred from the accessory to the tissue. Generally, high temperatures occur at the edge such that insulation materials such as silicone elastomers, fluorinated compounds (e.g., PTFE or PFA), and polyimids cannot be used directly on the metal as an insulator. The '305 patent discloses first applying one or more ceramic materials to coat the metal near the edge and then coating the ceramic with another material, such as a silicone elastomer or a fluorinated compound. These configurations require manufacturing process and materials selection that ensure adhesion of the coating material to the ceramic. While effective, such steps can add cost and complexity.

SUMMARY OF THE INVENTION

Accordingly, a primary objective of the present invention is to provide an apparatus and method for use in electrosurgery that has a durable coating that results in reduced generation of smoke at a surgical site.

Another objective of the present invention is to provide an apparatus and method for use in electrosurgery that yields less eschar accumulation on the electrosurgical instrument utilized.

An additional objective of the present invention is to provide an apparatus and method for use in electrosurgery that provides for reduced charring along an electrosurgical incision.

Yet another objective is to realize one or more of the foregoing objectives in a manner which does not significantly impact space or cost requirements, and which maintains and potentially enhances the effectiveness of electrosurgical procedures.

In addressing these objectives, the inventors have recognized that a relatively thin, substantially sealed insulating layer capable of withstanding the temperatures generated during electrosurgery can be provided on the surface(s) of metal elements comprising electrosurgical instruments. By way of primary example, the insulating layer may comprise a porous, adherent insulating material sealed with a sealing material that reduces accumulation of tissue or thermal decomposition products resulting therefrom. As will be described, the insulating layer provides both thermal insulation and electrical insulation.

In one aspect, it is preferable that the sealed insulating layer be less than 0.010 inches thick so that the overall thickness of the surgical instrument does not become so great as to interfere with surgical techniques. In another aspect, to achieve substantial thermal insulation while remaining relatively thin, the insulating layer benefits from the inclusion of an insulating material having a multiplicity of pores so that the insulating layer constituents have relatively poor or infrequent surface contact with each other to thereby reduce their ability to conduct thermal energy, and so that the sealing material may penetrate the insulating material at least at an outer surface of the insulating layer.

More particularly, pores of the insulating material may generally have a distribution of shapes and sizes. Considering an individual pore as being theoretically able to surround a sphere of a maximum diameter and defining the size of the pore as being such maximum diameter, it is preferable that the porous, insulating material have at least 10 percent of the pores preferably larger than about 50 nanometers, and more preferably have at least 10 percent of the pores larger than 0.05 micrometer, and still more preferably have at least 10 percent of the pores larger than about 0.5 micrometer. Preferably the insulating material has a maximum pore size less than about 50 micrometers, and more preferably the insulating material has a maximum pore size less than about 25 micrometers.

It is preferable for the sealing material to comprise a substantially hydrophobic material. Further, it is preferable that the sealing material at least partially penetrate the insulating material and be cured, thus forming a crosslinked material that seals the outer surface of the insulating layer. The seal reduces or prevents penetration of biologic materials or their decomposition products into the surface or into the pores of the insulating material. By way of example, the sealing material may preferably penetrate at least 10% of the thickness of the first insulating layer. To facilitate penetration, the sealing material may have a kinematic viscosity (e.g. dynamic viscosity/density) of about 3000 cSt (i.e. centistokes) or less, more preferably about 1500 cSt or less, even more preferably about 350 cSt or less, and most preferably about 200 cSt or less. In one embodiment, a sealing material having a kinematic viscosity of less than about 150 cSt has been employed.

The sealing material may be separately applied to an insulating material coated upon a metallic element(s), then cured to achieve sealing. Alternatively, the sealing material may be mixed with the insulating material, applied to a metallic element, then cured.

For best results, the insulating layer is selected so that it withstands the temperatures that exist during use of the electrosurgical instrument. In this regard, the insulating material may advantageously comprise one or more ceramic materials.

It may be noted that the pores of the insulating material, including in particular those made from porous ceramics, are generally not visible, even under considerable magnification. That the insulating material is porous may be determined by its color changing after it has been soaked in and then removed from a clear material, such as a clear or substantially clear liquid consisting of one or more polydiorganosiloxanes (e.g., approximately 100 cSt polydimethylsiloxane) or a derivative thereof, such as materials consisting of or made from one or more polydiorganosiloxanes and solvents.

It is believed that in the present invention the insulating material provides a thermal barrier that reduces the temperature experienced by the sealant, thus reducing or preventing thermal breakdown of the sealant, even if the sealant is a polysiloxane or a fluoropolymer such as PTFE. It is further believed that the cured sealant, particularly if it penetrates a ceramic insulating material layer, helps bond the ceramic to itself and to the metal element(s). The result is an insulating layer that is more durable and suitable for use with surgical instruments than either the ceramic or the sealant alone.

In one embodiment, the insulating layer may comprise a porous, adherent ceramic material that has had at least the pores on the surface sealed to prevent or impede the penetration of biological materials, water, saline, or other materials into the pores. Said ceramic may be applied to the metal element via dipping, spraying, brushing, or other means that applies ceramic to at least a portion of the surface, then cured via drying, firing, baking, or other curing means. Preferably, the ceramic insulating layer should be able to withstand temperatures of at least about 2000° F. The ceramic insulating layer may comprise various metal/non-metal combinations, including for example compositions that comprise in whole or in part one or more of the following: aluminum oxides (e.g. alumina and $Al_2O_3$), zirconium oxides (e.g. $Zr_2O_3$), zirconium nitrides (e.g. ZrN), zirconium carbides (e.g. ZrC), boron carbides (e.g. $B_4C$), silicon oxides (e.g. $SiO_2$), mica, magnesium-zirconium oxides (e.g. (Mg—Zr)$O_3$), zirconium-silicon oxides (e.g. (Zr—Si)$O_2$), titanium oxides (e.g., $TiO_2$) tantalum oxides (e.g. $Ta_2O_5$), tantalum nitrides (e.g. TaN), tantalum carbides (e.g., TaC), silicon nitrides (e.g. $Si_3N_4$), silicon carbides (e.g. SiC), tungsten carbides (e.g. WC) titanium nitrides (e.g. TiN), titanium carbides (e.g., TiC), nibobium nitrides (e.g. NbN), niobium carbides (e.g. NbC), vanadium nitrides (e.g. VN), vanadium carbides (e.g. VC), and hydroxyapatite (e.g. substances containing compounds such as $3Ca_3(PO_4)_2Ca(OH)_2Ca10$ $(PO_4)_6$ $(OH)_2Ca5(OH)(PO_4)_3$, and $Ca_{10}H_2O_{26}P_6$).

One or more ceramic layers may be employed to define the insulating material of the insulating layer, wherein one or more layers may be porous, such as holes filled with one or more gases or vapors. Such porous compositions will usually have lower thermal conductivity than nonporous materials. An example of such materials are foam e.g., an open cell silicon carbide foam, ceramics applied using plasma spray, flame spray, physical vapor deposition, chemical vapor deposition, or ceramics employing binders employing silicon-oxygen bonds. Such binders include alkali metal silicates (such as lithium polysilicate, potassium silicate, or sodium silicate), colloidal silica, colloidal alumina, or are made using preceramic polymers (such as polysilazanes, polyureasilazanes, silsesquioxanes, polydiorganosiloxanes, or polysiloxane resins), or silanes that have been at least partially hydrolyzed (including hydrolysis, acid hydrolysis, or alkali hydrolysis of alkytrialkylsilanes, including methyltrimethoxysilane, or dialkyldialkylsilanes) and at least partially condensed to form polydiorganosiloxanes. Ceramics using such binders employ one or more fillers to modify properties, such as thermal conductivity, bonding to substrates, porosity, and viscosity. Such fillers may include, but are not limited to, materials containing aluminum silicates (including clays, such as kaolin clay and smectite clays), magnesium silicates (including talc), metal oxides (including aluminum oxides, titanium dioxide, chrome oxide), and fibers (including fibers containing one more of aluminum oxide, silicon dioxide, calcium silicates). Such porous materials have the disadvantage that they allow fluids, vapors, or solids to enter the pores whereby they are exposed to prolonged contact with high temperatures which can lead to thermal decomposition or oxidation and produce smoke or other noxious or possibly dangerous materials. Sealing the outer surface of the ceramic insulating material(s) prevents such incursions, while substantially preserving the beneficial reduced thermal conductivity of the pores.

If electrosurgical devices such as blades are too thick then they do not perform well. Sealing a porous, ceramic insulating material is accomplished not by coating the ceramic in the sense that electrosurgical accessories have been coated with fluorinated compounds (e.g., PTFE, PFA), silicone elastomers (e.g., polydiorganosiloxane elastomer), and other such materials. Best surgical performance occurs when accessories are thin, therefore pores are best filled by a sealing material that penetrates the surface of the porous insulating material and seals the pores. Some residual sealant material may remain on the surface. It is beneficial for the sealant to be hydrophobic so that the outer surface of the sealed insulating layer resists accumulating biologic materials.

Sealing materials should preferably withstand temperatures exceeding 400° F. and more preferably withstand temperatures exceeding 500° F. Silicates and solutions containing or forming silicates upon curing are the preferred materials. Other materials may be used, including silicone and fluorosilicones. For sealing, the materials need to have low viscosity and other properties that enable penetration into the surface of the porous insulator. Traditional silicone and fluorosilicone elastomer-forming compounds do not have these properties unless they are extensively diluted with a thinning agent, such as xylene or acetone.

The sealed insulating layer may be advantageously employed to yield an average maximum thermal conductivity of about 0.009 W/cm-° K. or less when measured at 300° K. The insulating layer coating may preferably have a thickness of between about 0.001 and 0.01 inches, and most preferably between about 0.002 and 0.004 inches.

In further addressing the above-noted objectives, the present inventors have previously recognized that a large portion of the smoke generated utilizing known electrosurgical instruments results from the transmission of electrosurgical energy to tissue from areas of known electrosurgical instruments that are actually intended to be "non-functional" for purposes of achieving the desired electrosurgical effect (i.e. cutting or coagulation). That is, while known electrosurgical instruments include "functional" portions which are designed to be selectively positioned to direct an electrosurgical signal to an intended surgical location (e.g. along a desired incision line), the discharge of energy is not effectively restricted to the functional portions.

More generally in this regard, energy discharge from electrosurgical instruments may be in the form of electrical energy and/or thermal energy. Electrical energy is transferred whenever the electrical resistance of a region between an electrosurgical instrument and tissue can be broken down by the voltage of the electrosurgical signal. Thermal energy is transferred when thermal energy that has accumulated in the electrosurgical instrument overcomes the thermal resistance between the instrument and the tissue (i.e. due to temperature differences therebetween).

The discharge of electrical and thermal energy from nonfunctional areas of known electrosurgical instruments results in unnecessary heating of tissue at a tissue site. In the case of electrical energy discharge, thermal energy is generated as a result of tissue resistance. As the amount of thermal energy at a tissue site increases, the electrical resistance at the surgical site also increases, thereby resulting in the further generation of heat. Such increased heating may in turn result in tissue charring as well as the splattering of tissue matter onto the electrosurgical instrument employed. The splattered tissue matter may accumulate as eschar on the electrosurgical instrument and present a further resistance/heat source to the surgical site. Eschar accumulation on electrosurgical instruments also raises the need for medical personnel to periodically suspend a procedure in order to clean the eschar from the electrosurgical instrument. As can be appreciated, such disturbances can adversely impact an electrosurgical procedure.

In short, the present inventors have previously recognized that any undesired and unnecessary discharge of electrosurgical energy from non-functional portions of an electrosurgical instrument to a surgical site can have a negative and cascading effect of unnecessary heat generation and resultant smoke generation, eschar build-up on the electrosurgical instrument and unnecessary tissue charring. In the later regard, it is believed that tissue charring may adversely affect healing.

In conjunction with the above-referenced recognition, the present invention provides an apparatus and method for reducing unnecessary/undesired electrical and/or thermal discharge during electrosurgical procedures. Such reduction (s) are achieved via enhanced localization of electrical and thermal energy transmission to a tissue site. More particularly, the present invention markedly reduces electrical/thermal discharge from non-functional areas of an electrosurgical instrument by insulating the nonfunctional areas, and optionally, by providing for an effective level of heat removal away from functional portions of an electrosurgical instrument and/or by otherwise enhancing the localized delivery of an electrosurgical signal to a tissue site.

In this regard, the present invention comprises an electrosurgical instrument having at least one metal element that may be defined by metal body for carrying an electrosurgical signal and an outer insulating layer positioned over at least a portion of the metal body (i.e., a non-functional portion). The metal body may include a main body portion and a peripheral edge portion, the peripheral edge portion being functional for the conveyance of the electrosurgical signal to a tissue site.

In a further aspect of the present invention, the outer insulating layer may be advantageously provided to have a maximum thermal conductance of about 1.2 W/cm$^2$-° K when measured at about 300° K., more preferably about 0.12 W/cm$^2$-° K. or less when measured at about 300° K., and most preferably about 0.03 W/cm$^2$-° K. when measured at about 300° K. For purposes hereof, thermal conductance is intended to be a measure of the overall thermal transfer across any given cross section (e.g. of the insulation layer), taking into account both the thermal conductivity of the materials comprising such layer and the thickness of the layer (i.e. thermal conductance of layer=thermal conductivity of material comprising the layer (W/cm° K.)/thickness of the layer (cm)). In relation to the foregoing aspect, the insulation layer should also exhibit a dielectric withstand voltage of at least the peak-to-peak voltages that may be experienced by the electrosurgical instrument during surgical procedures. The peak voltages will depend upon the settings of the RF source employed, as may be selected by clinicians for particular surgical procedures. For purposes of the present invention, the insulation layer should exhibit a dielectric withstand voltage of at least about 50 volts, and more preferably, at least about 150 volts. As employed herein, the term dielectric withstand voltage means the capability to avoid an electrical breakdown (e.g. an electrical discharge through the insulating layer).

In another aspect of the present invention, while a metal body of the inventive electrosurgical instrument may comprise stainless steel, it may be more preferable for the metal body to comprise a metal that yields a thermal conductivity of at least about 0.35 W/cm° K. when measured at about 300° K. By way of primary example, the metal body may advantageously comprise at least one metal selected from a group comprising: silver, copper, aluminum, gold, tungsten, tantalum, columbium (i.e., niobium), and molybdenum. Alloys comprising at least about 50% (by weight) of such metals may be employed, and even more preferably at least about 90% (by weight). Additional metals that may be employed in such alloys include zinc.

In yet another aspect of the present invention, at least a portion of the peripheral edge portion of the metal body is not insulated (i.e. not covered by the outer insulating layer). In connection therewith, when the outer peripheral edge portion comprises a material that is not bicompatible, (e.g., copper) such portion may be coated (e.g. about 10 microns or less) with a biocompatible metal. By way of example, such biocompatible metal may be selected from the group comprising: nickel, silver, gold, chrome, titanium tungsten, tantalum, columbium (i.e., niobium), and molybdenum.

In an additional aspect of the invention, it has also been determined that a reduced cross-section, (such as a laterally tapered, or sharpened) uninsulated peripheral edge portion having a maximum cross-sectional thickness which is less than about 1/10 of the maximum cross-sectional thickness of the main body portion is particularly effective for achieving localized electrosurgical signal delivery to a tissue site. In the later regard, it has also been determined preferable that the outer extreme of the peripheral edge portion of the metal body have a thickness of about 0.001 inches or less.

In an additional related aspect of the present invention, the metal body may comprise two or more layers of different materials. More particularly, at least a first metal layer may be provided to define an exposed peripheral edge portion of the metal body that is functional to convey an electrosurgical signal to tissue as described above. Preferably, such first metal layer may comprise a metal having a melting temperature greater than about 2600° F., more preferably greater than about 3000° F., and even more preferably greater than about 4000° F., thereby enhancing the maintenance of a desired peripheral edge thickness during use (e.g. the outer extreme edge noted above). Further, the first metal layer may preferably have a thermal conductivity of at least about 0.35 W/cm° K. when measured at 300° K.

For living human/animal applications, the first metal layer may comprise a first material selected from a group consisting of tungsten, tantalum, columbium (i.e., niobium), and molybdenum. All of these metals have thermal conductivities within the range of about 0.5 to 1.65 W/cm° K. when measured at 300° K. Preferably, alloys comprising at least about 50% by weight of at least one of the noted first materials may be employed, and even more preferably at least about 90% by weight.

In addition to the first metal layer the metal body may further comprise at least one second metal layer on the top and/or bottom of the first metal layer. Preferably, a first metal layer as noted above is provided in a laminate arrangement between top and bottom second metal layers. To provide for rapid heat removal, the second metal layer(s) preferably has a thermal conductivity of at least about 2 W/cm° K. By way of primary example, the second layer(s) may advantageously comprise a second material selected from a group consisting of copper, gold, silver and aluminum. Preferably, alloys comprising at least about 50% of such materials may be employed, and even more preferably at least about 90% by weight. It is also preferable that the thickness of the first metal layer and of each second metal layer (e.g. for each of a top and bottom layer) be defined at between about 0.001 and 0.25 inches, and even more preferably between about 0.005 and 0.1 inches.

As may be appreciated, multi-layered metal bodies of the type described above may be formed using a variety of methods. By way of example, sheets of the first and second materials may be roll-bonded together then cut to size. Further, processes that employ heat or combinations of heat and pressure may also be utilized to yield a laminated metal body.

In a further aspect of the present invention, the inventive electrosurgical instrument may further comprise a heat sink for removing thermal energy from the metal body. In this regard, the provision of a heat sink establishes a thermal gradient away from the peripheral edge of the metal body, thereby reducing undesired thermal transfer to a tissue site. More particularly, it is preferable for the heat sink to operate so as to maintain the maximum temperature on the outside surface of the insulating layer at about 160° C. or less, more preferably at about 80° C. or less, and most preferably at 60° C. or less. Relatedly, it is preferable for the heat sink to operate to maintain an average metal body temperature of about 500° C. or less, more preferably of about 200° C. or less, and most preferable of about 100° C. or less.

In one approach, the heat sink may comprise a vessel comprising a phase change material that either directly contacts a portion of the metal body (e.g. a support shaft portion) or that contacts a metal interface provided on the vessel which is in turn in direct contact with a portion of the metal body (e.g. a support shaft portion). Such phase change material changes from a first phase to a second phase upon absorption of thermal energy from the metal body. In this regard, the phase change temperature for the material selected should preferably be greater than the room temperature at the operating environment and sufficiently great as to not change other than as a consequence of thermal heating of the electrosurgical instrument during use. Such phase change temperature should preferably be greater than about 30° C. and most preferably at least about 40° C. Further, the phase change temperature should be less than about 225° C. Most preferably, the phase change temperature should be less than about 85° C.

The phase change may be either from solid to liquid (i.e., the phase change is melting) or from liquid to vapor (i.e., the phase change is vaporization) or from solid to vapor (i.e., the phase change is sublimation). The most practical phase changes to employ are melting and vaporization. By way of example, such phase change material may comprise a material that is an organic substance (e.g., fatty acids such as stearic acid, hydrocarbons such as paraffins) or an inorganic substance (e.g., water and water compounds containing sodium, such as, sodium silicate (2-)-5-water, sodium sulfate-10-water).

In another approach, the heat sink may comprise a gas flow stream that passes in direct contact with at least a portion of the metal body. Such portion may be a peripheral edge portion and/or a shaft portion of the metal body that is designed for supportive interface with a holder for hand-held use. Alternatively, such portion may be interior to at least a portion of the metal body, such as interior to the exposed peripheral edge portion and/or the shaft portion of the metal body that is designed for supportive interface with a holder for hand-held use. In yet other approaches, the heat sink may simply comprise a thermal mass (e.g. disposed in a holder).

In one arrangement of the present invention, an electrosurgical instrument comprises a main body portion having a blade-like configuration at a first end and an integral, cylindrical shaft at a second end. The main body may comprise a highly-conductive metal and/or multiple metal layers as noted. At least a portion of the flattened blade end of the main body is coated with a sealed, ceramic-based insulating layer, except for the peripheral edge portion thereof. The cylindrical shaft of the main body is designed to fit within an outer holder that is adapted for hand-held use by medical personnel. Such holder may also include a chamber comprising a phase-change material or other heat sink as noted hereinabove. Additionally, electrical, push-button controls may be incorporated into the holder for selectively controlling the application of one or more, predetermined, electrosurgical signal(s) from an RF energy source to the flattened blade via the shaft of the main body portion.

In the latter regard, conventional electrosurgical signals may be advantageously employed in combination with one or more of the above-noted electrosurgical instrument features. In particular, the inventive electrosurgical instrument yields particular benefits when employed with electrosurgical signals and associated apparatus of the type described in U.S. Pat. No. 6,074,387, hereby incorporated by reference in its entirety.

Numerous modifications and additions to the present invention will be apparent to those skilled in the art upon consideration of the further description that follows.

DETAILED DESCRIPTION OF THE INVENTION

Figure 1:
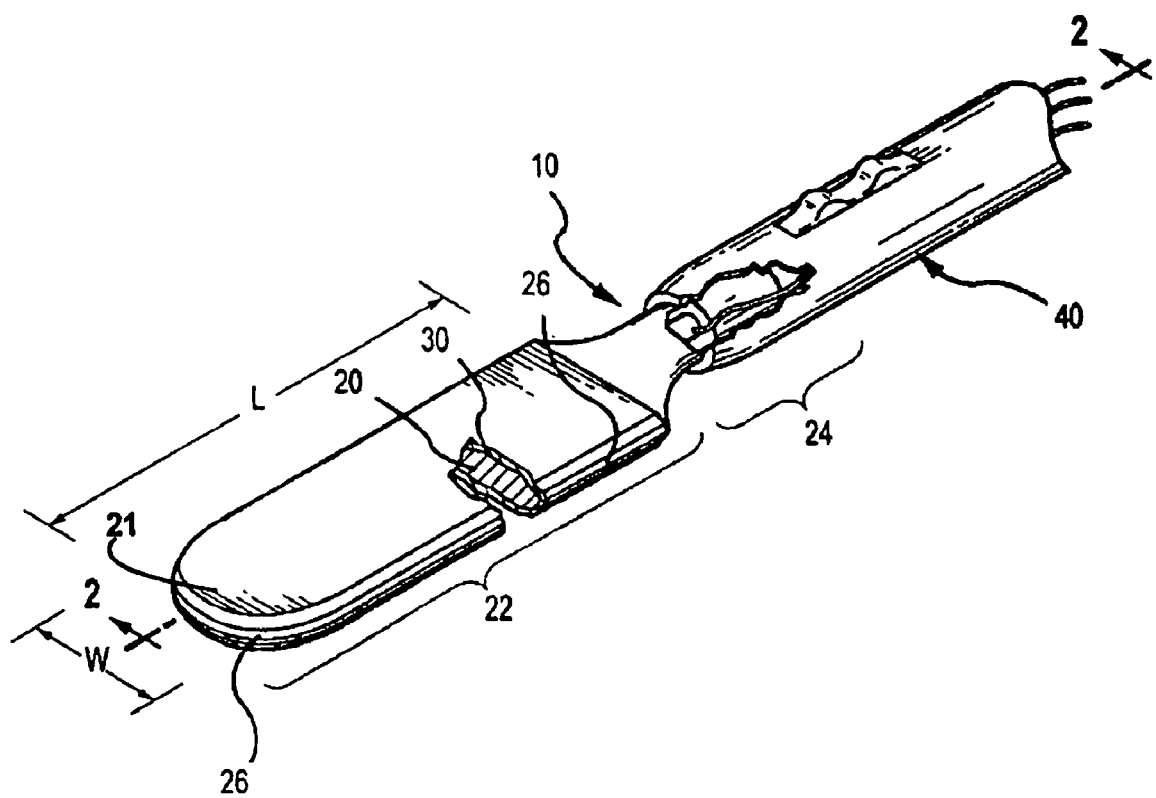
FIG. 1 illustrates a perspective, partial cut-away view of an electrosurgical instrument in one embodiment of the present invention.
Figure 2:
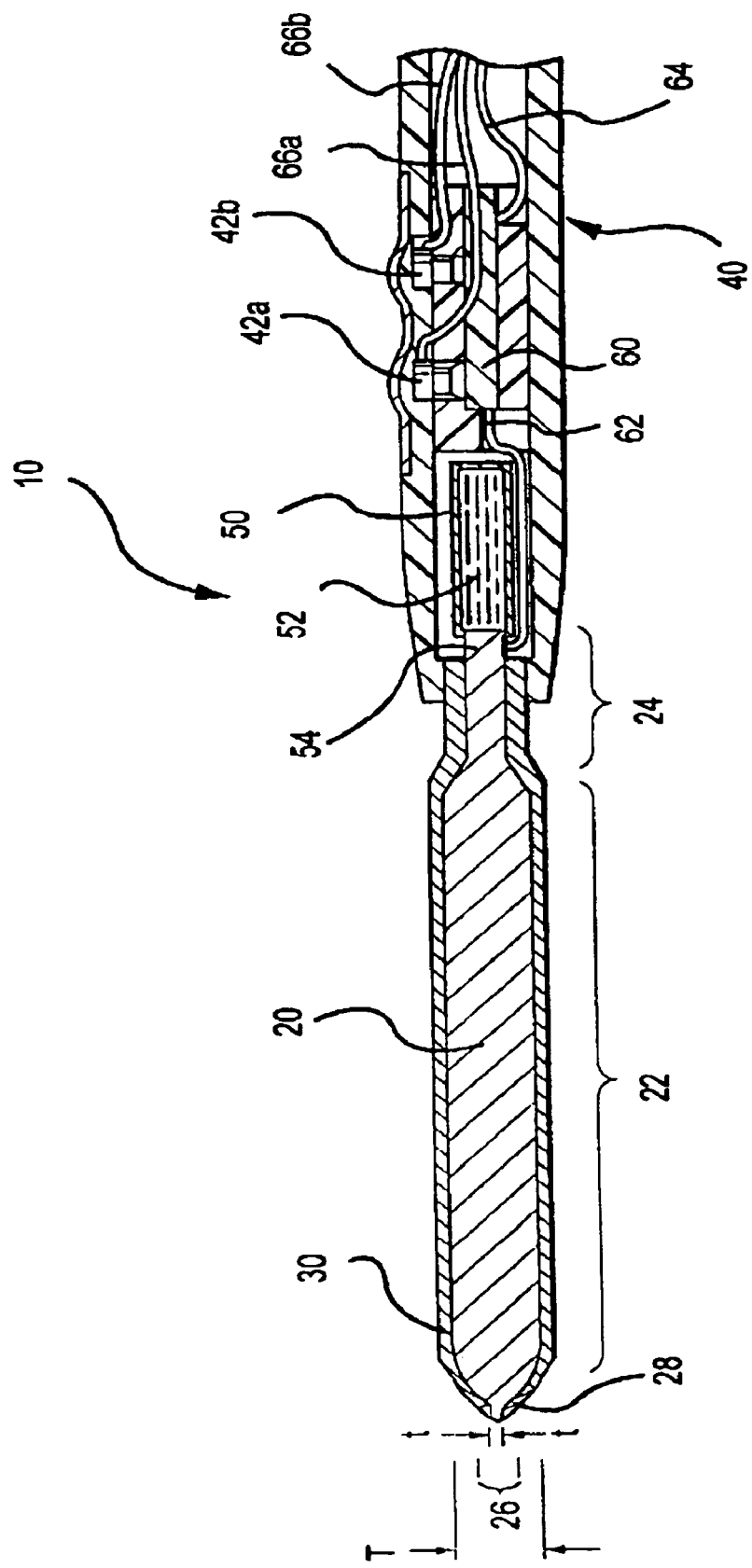
FIG. 2 illustrates a side, cross-sectional view of the electrosurgical instrument embodiment of FIG. 1

FIGS. 1 and 2 illustrate one embodiment of an electrosurgical instrument having a blade-like, pencil configuration. As will be appreciated, the present invention may also be readily embodied in other instrument configurations, including for example, ball electrodes and forceps.

As illustrated in FIGS. 1 and 2, the electrosurgical instrument 10 includes a main body 20 having an outer, insulating layer 30. Insulating layer 30 comprises a porous, insulating material, or coating, that has been sealed. The main body 20 includes a flattened, distally-extending blade portion 22 and a proximally-extending cylindrical shaft portion 24. The blade portion 22 has a reduced cross-section laterally outward (i.e., in cross-sectional thickness), such reduction being made either continuously, for example, by tapering, or using one or more steps, to produce a relatively thin outer peripheral edge about at least a distal tip 21 to define peripheral edge portion 26. In the illustrated embodiment the distal tip 21 is rounded but other reduced width profiles such as those that came approximately to a point or corner, including those that are not symmetric, may be used. In the illustrated embodiment, peripheral edge portion 26 is not covered by insulating layer 30. In other embodiments one or more portions of peripheral edge portion 26 may be covered by insulation while leaving one or more portions of peripheral edge portions not covered by insulation. Preferably, peripheral edge portion 26 has outer extreme edge thickness t of about 0.001 inches or less. Further, the maximum thickness of edge portion 26 is preferably no more than about 1/10 of the maximum thickness T of main body 20.

The main body 20 should substantially comprise a metal. In this regard, while stainless steel and/or other similar metals may be employed, it may be preferable for main body 20 to comprise a metal having a relatively high thermal conductivity (e.g. at least about 0.35 W/cm° K. when measured at 300° K.). In particular, main body 20 may advantageously comprise a metal selected from the group comprising: copper, silver, gold, aluminum, tungsten, tantalum, columbium and molybdenum. Alloys of such metals (e.g., at least about 50% by weight), may also be employed. The use of such metals in the main body 20 allows for not only effective delivery of an electrosurgical signal there through for transmission via peripheral edge portion 26 to a tissue site, but additionally facilitates the removal of heat rearwardly away from peripheral edge portion 26 during operation. Such heat removal reduces undesired heat transfer from the electrosurgical instrument 10 to a tissue site during use. In the event copper is utilized for main body 20 in the FIG. 1 embodiment, a biocompatible plating 28 (e.g. nickel, gold, silver, chrome or titanium) may be selectively applied to peripheral edge 26.

The insulating layer 30 should provide both thermal and electrical insulation capabilities so as to reduce the discharge of thermal and electrical energy, respectively, from electrosurgical instrument 10 during use. For example, the outer insulating layer 30 should most preferably comprise a material having a thermal conductivity of about 0.009 W/cm-° K. or less when measured at about 300° K. Further, the insulation layer should exhibit a dielectric withstand voltage of at least about 50 volts, and more preferably at least about 150 volts.

By way of example, layer 30 may comprise a ceramic insulating material with a metal oxide-based, such as silicon dioxide-based, binder that is sealed with a silicon-based, polymeric material. Examples of binders are materials that contain substances that produce interconnected silicon-oxygen bonded lattices or networks. Such binders include alkali metal silicates (such as lithium polysilicate, potassium silicate, or sodium silicate), colloidal silica, colloidal alumina, or are made using preceramic polymers (such as polysilazanes, polyureasilazanes, silsesquioxanes, polydiorganosiloxanes, polysiloxane resins), metal siliconate (such as an alkylsiliconate, e.g., potassium methyl siliconate), or silanes that have been at least partially hydrolyzed (including hydrolysis, acid hydrolysis, or alkali hydrolysis of alkytrialkylsilanes, including methyltrimethoxysilane, or dialkyldialkylsilanes) and at least partially condensed to form polydiorganosiloxanes. In particular, Ludox brand colloidal silicas and alkali metal silicates (Grace Davison division of W.R. Grace & Co., Columbia, Md.), and Megasol brand colloidal silicas (Wesbond Corporation, Wilmington, Del.)

may be used, with colloidal silica binders being preferred because they produce ceramics with better durability than those using alkali metal silicates. An example preceramic polymer that produced satisfactory results is GE SS4004P (GE Silicones, Waterford, N.Y.). An example silane that produces a binder when hydrolyzed and partially condensed is Dow Corning Z6070 (Dow Corning, Midland, Mich.).

Mixed with the binder are fillers that alter properties such as thermal conductivity, bonding to substrates, viscosity, porosity, and structural integrity. Such fillers may include, but are not limited to, materials containing aluminum silicates (including clays, such as kaolin clay and smectite clays), magnesium silicates (including talc), metal oxides (including aluminum oxides, titanium dioxide, chrome oxide), and fibers (including fibers containing one more of aluminum oxide, silicon dioxide, calcium silicates). Examples of fillers are EPK kaolin and Pioneer talc (both supplied by Zemex Industrial Minerals, Atlanta, Ga.), Nyglos 2 brand of wollastonite (Nyco Minerals, Inc., Willsboro, N.Y.), and RF50/99 aluminum oxide/silica fiber (Saint-Gobain TM K.K, Tokyo, Japan). As will be appreciated, various combinations of materials can lead to materials with a range of properties that make mixtures more, or less, suitable for applying the insulating material coating using various means such as dipping, brushing, or spraying and that the process parameters, such as withdrawal rate for dipping and nozzle size and pressure for spraying, affect the thickness, uniformity, and properties of the coatings.

Insulating layers that are too thick, particularly at the edge where electrosurgical energy transfers to tissue, interfere with the surgical process. Sealed ceramic coatings thinner than 0.010 inches are preferred and sealed ceramic coatings between about 0.002 and 0.004 are more preferred. The peripheral edge portion 26 that is preferably not insulated. Immediately adjacent to the peripheral edge portion 26, sealed ceramic coatings with thicknesses between 0.001 and 0.003 are preferred.

Example ceramic formulations, in weight percent, for dip coating are:
(1) 54% Megasol S50 (Wesbond Corporation), 23% RF50/99 fiber, 23% Pioneer talc.
(2) 49% GE SS4004P, 15% RF50/99 fiber, 35% EPK kaolin,
(3) 55% Dow Corning Z6070, 20% distilled water, 17% EPK kaolin, 8% Nyglos 2.

After mixing the components for at least one hour, a clean metal device, such as an electrosurgical blade, is dipped into the ceramic mixture, the peripheral edge portion 26 that is not to have ceramic coating is scraped free of liquid, and then dried with an orientation, typically edge up, such that ceramic does not flow over the edge while the coating is still fluid. After drying, the part is baked at approximately 200° F. to 550° F. for between 30 minutes and 12 hours. The baking process facilitates bonding the ceramic to the metal substrate, such as molybdenum, and cures the ceramic.

For sealing purposes, porous ceramic coating is desired, although the pores may be sufficiently minute as to not be visible, even under substantial magnification. Whether the ceramic coating is sufficiently porous can be determined by soaking it in a clear penetrating substance, such as 100 cSt polydimethylsiloxane oil, and noting whether the color of the ceramic changes. If the color changes it is due to the coating taking up the penetrating substance into the ceramic's pores.

After the ceramic has been cured the seal coat is applied. As noted earlier, the preferred seal coat is a substantially hydrophobic material, such as a fluorinated polymer, such as PFTE or PFA, or a polysiloxane or a material made from a polysiloxane. Preferably, the sealant forms a material having a high contact angle with water, e.g. about 90° or more, and cures to a durable film.

The seal coat is preferably formed from a liquid that penetrates the ceramic coating during a reasonably short time, such as less than 30 minutes. To promote this penetration, it is best if the seal coat material has a kinematic viscosity preferably less than 350 cSt and more preferably less than 200 cSt and still more preferably about 150 cSt or less. These viscosities are at the temperature at which the sealant is applied to the ceramic. For example, the application temperature may be greater than room temperature in order to reduce the viscosity of materials that are too viscous for adequate penetration into the ceramic when applied at room temperature. By way of example, a metallic part with a porous ceramic coating may be dipped in a liquid sealing material, withdrawn such that a liquid remains on the ceramic coating, and then placed in a warm oven where the remaining liquid warms and has its viscosity reduced such that it more readily penetrates the porous ceramic coating.

Example PTFE materials are the solvent-based XYLAN 8820HR (Whifford Corporation, West Chester, Pa.) and the water-borne Dupont 307A. The XYLAN 8820 HR requires considerable dilution to reduce its viscosity, and even then its penetration is generally slight and over most of the surface the coating is most notable as a surface coat. However, near edges the XYLAN shrinks back after curing leaving no visible surface treatment, but the ceramic remains sealed and hydrophobic. Dupont 307A has a low viscosity (about 20 cSt), small particle size (about 0.05 to 0.5 micrometers), contains wetting agents, and readily wets and penetrates surfaces with sufficiently large pores, although it will typically also produce a noticeable surface coating.

The preferred sealants are polydiorganosiloxanes or materials derived from these silicones. Representative classes of useful silicones include, for example, polydimethylsiloxane oils, solutions of silicone resins in hydrocarbon solvents and dilute aqueous solutions of siliconates. These include siloxanes with functional groups, such as amino or hydroxy functional groups, that promote bonding to metals. The preferred silicones are the polysiloxanes, in particular the polyalkylsiloxanes. A preferred polyalkylsiloxane is polydimethylsiloxane. Examples are aminofunctional siloxanes or hydroxyfunctional siloxanes. Example commercial polydimethyl siloxane products are MED-360, MED-361, MED-420 (NuSil Technology, Carpinteria, Calif.). Further example products are the aminofunctional polydimethylsiloxane dispersions MDX4-4159 (Dow Corning, Midland Mich.) and MED-4159 (NuSil Technology). A further example product is the hydroxy-terminated polydimethylsiloxane MED-4162 (NuSil Technology). An example of a solvent dispersed polydiorganosiloxane resin is Cotronics 1529 (Cotronics Corporation, Brooklyn, N.Y.). Water-borne dispersions of polydiorganosiloxanes, such as Dow Corning 365, may also be suitable.

The preferred means for applying the seal coat material is by soaking the ceramic-coated part in the sealant. Although penetration may be aided by soaking in a vessel that has a pressure less than ambient pressure to facilitate outgassing, such vacuums are not required when using low viscosity sealants, such as those having kinematic viscosities under about 200 cSt and preferably about 150 cSt or less. Soaking is complete when the parts have a uniform change in color or appearance. Often the change in appearance resembles making the ceramic coating appear almost transparent. After soaking, peripheral edge 20 is preferably lightly scraped to remove seal coat from the edge to prevent an insulating film from forming. Curing is then done. The cure is selected to promote polymerization of the sealant and produce a hard durable material. A typical cure when using MDX4-4159 is air drying for about two hours followed by about 1 hour ramping up from room temperature to 276° C. (536° F.) followed by 1 to 2 hours dwell at temperature. Similar cures are used with other diorganosiloxanes.

When curing PTFE sealants the sealant typically dries about 1 hour at room temperature, 1 hour at about 250° F., and then ramps up from 250° F. to about 680° F. over 30 to 45 minutes and then dwells at temperature for about 15 minutes.

Another embodiment for providing insulating layer 30 is to prepare a mixture of ceramic material and sealant material together and apply this combined mixture to main body 20 to form the sealed insulating layer 30. The ceramic material is preferably a powder or fiber. Said powders or fibers of ceramic materials may contain, for example, one or more aluminum silicate, magnesium silicate, calcium silicate, silicon dioxide or other metal oxide or other combination of a metal and a non-metal. Preferably, such ceramic powders or fibers have at least 50 percent by weight of the material having a diameter, length, or other measure of linear size that is less than 1000 micrometers and preferably less than about 100 micrometers. For example, a preceramic polymer, such as a polydiorganosiloxane or a derivative of such materials may be mixed with one or more powders or fibers of ceramic material. As another example, a PTFE dispersion, such as Dupont PTFE 307A, may be mixed with one or more powders or fibers of ceramic material. Particularly in the case where a water-borne dispersion is used, such as when a water-borne PTFE or PFA dispersion is used, a water-borne binder containing silicon-oxygen bonds, such as colloidal silica or an alkali-metal silicate, may also be included in the mixture. Preferably, when using a water-borne PFA or PTFE dispersion the weight percent of PFA or PTFE dispersion is between about 1 percent and 75 percent, and more preferably between about 5 and 60 percent, and more preferably between about 10 and 50 percent, and even more preferably between about 20 and 40 percent. As a further example, a diorganosiloxane or a material derived from such materials may be mixed with one or more powders or fibers of ceramic material and then applied to a substantially metallic element and cured. In this case a polydiorganosiloxane cures to form both a ceramic binder and a sealer. As an example, an aminofunctional dimethoxysilane copolymer dispersion, such as Dow Corning MDX4-4159, may be mixed with kaolin clay and talc powders and applied to a metal blade and then cured, e.g. 276° C. (536° F.) for 1 to 2 hours. When a diorganosiloxane or material derived from such materials is used the diorganosiloxane or material derived therefrom preferably constitutes a weight percent of between 5 and 95 percent of the mixture, and more preferably from between 20 and 80 percent of the mixture, and still more preferably between about 35 and 65 percent of the mixture applied to the metal elements of surgical instruments.

As best shown in FIG. 2, the shaft portion 24 of the main body 20 is supportably fitted into a forward end of an elongated holder assembly 40 that is adapted for hand-held use and manipulation by medical personnel. Such supportive interface may be either permanent (e.g. wherein the entire electrosurgical instrument 10 is disposed of after use), or the interface may be designed for selective insertion/removal of the main body 20 into/from welder assembly 40 (e.g. wherein the holder assembly 40 may be reused). In the embodiment of FIGS. 1 and 2, the holder assembly 40 houses a vessel 50 containing a phase change material 52. The vessel 50 is provided with a thermally conductive interface such as a thermally conductive pad 54, which may butt against the end of the shaft portion 24 of main body 20, as shown in FIG. 2, or which may partially or totally surround the shaft portion, at one end for direct contact and thermal interface with the end of shaft portion 24 of the main body 20.

The phase change material 52 may be selected to provide an effective heat sink for removal of thermal energy from main body 20. More particularly, the phase change material 52 may preferably maintain main body 20 at an average temperature of about 500° C. or less, more preferably at about 200° C. or less, and most preferably at about 100° C. or less. For such purposes, the phase change material may be provided to change from a first phase to a second phase (e.g., solid to liquid) at a predetermined temperature of at least about 40° C. Further, for the arrangement of FIG. 1, it has been found that when a 100 W signal is applied to main body 20, phase change material 52 should be capable of removing at least about 8 W of thermal energy.

By way of example, phase change material 52 may comprise a material that is an organic substance (e.g., fatty acids such as stearic acid, hydrocarbons such as paraffins) or an inorganic substance (e.g., water, and water compounds containing sodium, such as sodium silicate (2-)-5 water, sodium sulfate-10-water). Phase change material 52 may undergo phase changes of melting, vaporization, or sublimation, although melting and vaporization are preferred. Most preferably, the phase change temperature is greater than about 40° C. and less than about 85° C. While FIGS. 1-2 illustrate that phase change material 52 is contained within vessel 50, phase change material 52 may be alternatively disposed within and circulated through a sealed passageway within holder assembly 40.

The holder assembly 40 may further comprise one or more switch buttons 42a, 42b for the selective application of a predetermined electrosurgical signal to the main body portion 20. More particularly, switch button 42a may be depressed to electrically contact a metal plate 60, wherein an electrosurgical signal for tissue cutting may be provided to plate 60 and in turn to main body 20 via line 62. Similarly, switch button 42b may be depressed to electrically contact metal plate 60, wherein an electrosurgical signal for tissue coagulation may be provided to plate 60 and in turn main body 20 via line 62. Source signal line 64 as well as source signal return lines 66a and 66b may all be provided for receiving/returning signals to an RF electrosurgical source generator in a conventional fashion.

In one arrangement, electrosurgical instrument 10 comprises a blade portion 22 having a thickness T of about 0.020 inches (see FIG. 3), a width W of about 0.140 inches and length L of about 1 inch. In such arrangement, the main body 20 comprises copper (e.g., about 98% by weight) and insulating layer 30 has a thickness of less than 0.010 inches. Further, a phase change material comprises about 2 grams of stearic acid. This arrangement has been found particularly effective to yield reduced smoke generation and tissue charring.

Figure 3:
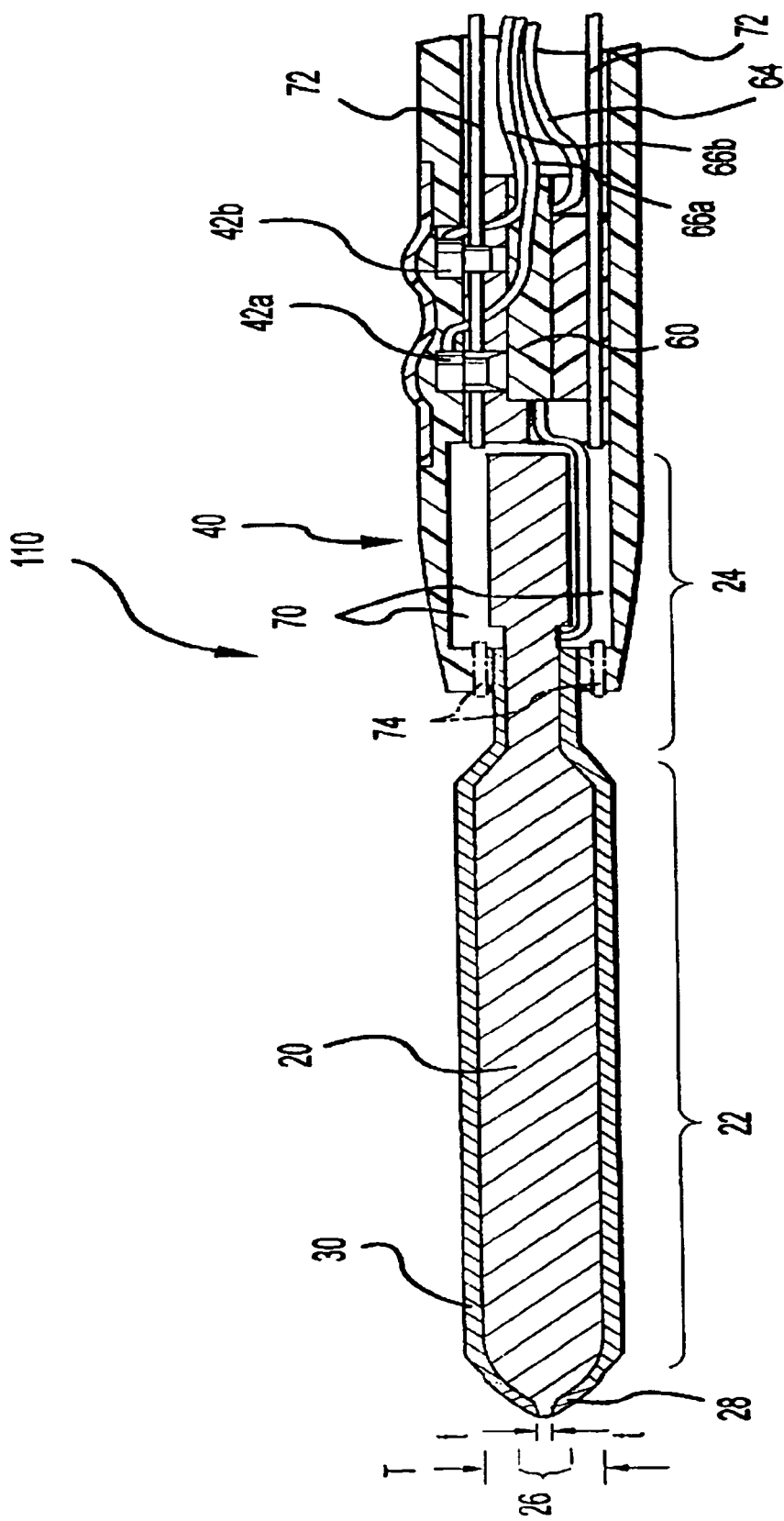
FIG. 3 illustrates a side, cross-sectional view of another electrosurgical instrument embodiment of the present invention.

FIG. 3 illustrates an alternate embodiment of an electrosurgical instrument 110 and is largely of the same construction as electrosurgical instrument 10 illustrated in FIGS. 1 and 2. As opposed to utilizing a phase change material 52 for the removal of thermal energy from main body 20, however, the embodiment illustrated in FIG. 3 utilizes a cooling gas stream that is circulated through an internal channel 70 of holder assembly 40 to remove thermal energy from shaft portion 24 of main body 20. As illustrated, channel 70 may be interconnected to a gas source via tubing lines 72 for circulation/cooling. In a modification of the embodiment shown in FIG. 3, channel 70 may be modified to pass directly on through conduits 74 at the forward extreme of holder assembly 70, and through an annular outlet 76 positioned immediately about the main body 20, wherein the cooling gas passing there through contacts the peripheral edge portion 26 for heat removal purposes. In yet other arrangements, the heat sink employed may utilize a liquid stream, a combination liquid/gas stream, gas and liquid streams that are separate (e.g., a heat pipe), and a thermal mass (e.g., a copper block).

Figure 4:
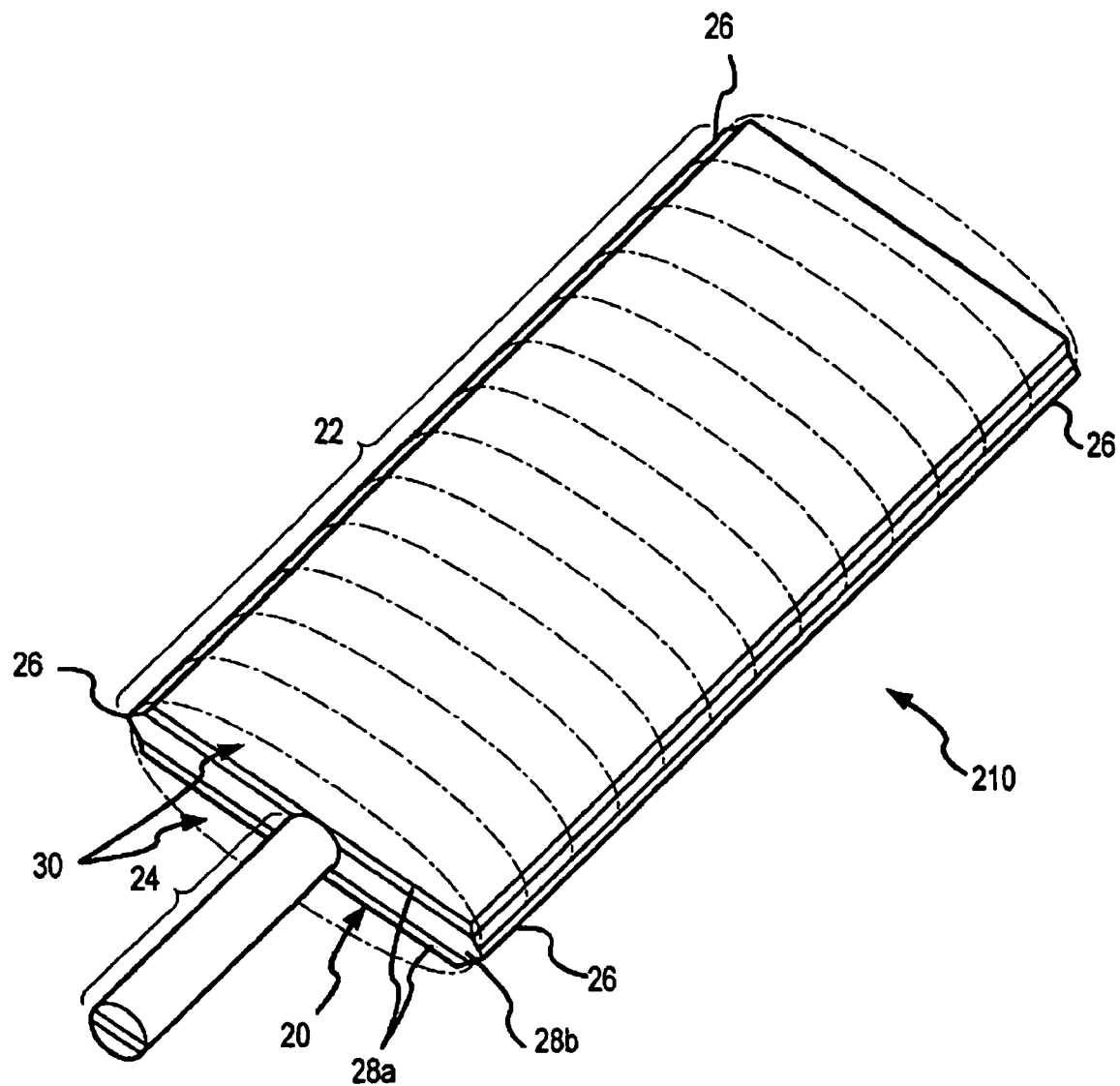
FIG. 4 illustrates a perspective view of yet another electrosurgical instrument embodiment of the present invention.

FIG. 4 illustrates a further alternate embodiment of an electrosurgical instrument 210. As shown, electrosurgical instrument 210 includes a main body 20 defined by a laminate structure consisting of top and bottom layers 28a and an intermediate layer 28b sandwiched therebetween. As illustrated, a peripheral edge portion 26 of the intermediate layer 28b is exposed (i.e., not covered by insulating layer 30). Preferably, such peripheral edge portion 26 has an outer, extreme edge thickness t of about 0.001 inches or less. Further, in the illustrated embodiment, the peripheral edge portion 26 is approximately centered about a center plane of the intermediate layer 28b. Such center plane may further coincide with a center plane of a blade portion 22 of the electrosurgical instrument 210.

The main body 20 preferably comprises metals which have a relatively high thermal conductivity (e.g., at least about 0.35 W/cm° K. when measured at 300° K.). For example, top and bottom layers 28a may preferably comprise one or more metal selected from a group consisting of gold, silver, aluminum and copper. Such materials have thermal conductivities of at least about 2 W/cm° K. when measured at 300° K. Further, intermediate layer 28b of the main body 20 preferably comprises a metal having a melting point of at least about 2600° F. In particular, intermediate layer 28b may comprise one or more materials from a group consisting of tungsten, tantalum, columbium and molybdenum. The intermediate layer 28b and the top and bottom layers 28a may preferably each have a thickness of between about 0.001 and 0.25 inches.

In one arrangement, electrosurgical instrument 210 may include a main body 20 with an intermediate layer 28b that comprises an alloy comprising at least about 95% molybdenum by weight. In such arrangement, top and bottom layers 28a may comprise a copper alloy containing at least about 95% copper by weight. The intermediate layer 28b and top and bottom layers 28a may each be defined at a thickness of between about 0.050 and 0.001 inches and more preferably each may be defined at a thickness of between 0.005 and 0.015 inches. Preferably, the total thickness of intermediate layer 28b and top and bottom layers 28a is less than about 0.030 inches and more preferably between about 0.010 and about 0.020 inches. While not shown, the shaft portion 24 in the described arrangement may interface with a heat sink (e.g., a thermal mass disposed within a handle portion).

Numerous additional embodiments and modifications will be apparent to those skilled in the art and are encompassed by the present invention as defined by the claims which follow.

What is claimed is:

1. An electrosurgical instrument, comprising:
at least one substantially metallic element; and,
an insulating layer positioned over at least a portion of the at least one substantially metallic element, said insulating layer including a porous insulating material and a sealing material, wherein said sealing is substantially hydrophobic, substantially seals at least an outer surface of said insulating material, and penetrates at least a portion of said porous insulating material.

2. An electrosurgical instrument as recited in claim 1, wherein said porous insulating material further comprises a metal-oxide based binder.

3. An electrosurgical instrument as recited in claim 1, wherein said porous insulating material comprises at least one ceramic material.

4. An electrosurgical instrument as recited in claim 1, wherein said insulating layer has a thickness of less than 0.01 inches.

5. An electrosurgical instrument as recited in claim 1, wherein said sealing material penetrates at least about 10% of a total thickness of said insulating layer.

6. An electrosurgical instrument as recited in claim 5, wherein said sealing material comprises at least one material from a group consisting of polydiorganosiloxanes and materials derived therefrom.

7. An electrosurgical instrument as recited in claim 1, wherein said at least one substantially metallic element includes: a metal body having a main body portion and a peripheral edge portion.

8. An electrosurgical instrument as recited in claim 7, wherein said metal body is laterally-tapered down in cross-sectional thickness from said main body portion to said peripheral edge portion.

9. An electrosurgical instrument as recited in claim 8, wherein said peripheral edge portion is not covered by said insulating layer.

10. An electrosurgical instrument as recited in claim 9, wherein said substantially sealed insulating layer has a thickness of less than 0.01 inches.

11. An electrosurgical instrument as recited in claim 10, wherein said peripheral edge portion has a thickness less than about 1/10 of the maximum cross-sectional thickness of the main body portion.

12. An electrosurgical instrument as recited in claim 9, wherein said insulating layer substantially covers the entirety of said metal body apart from said peripheral edge portion.

13. An electrosurgical instrument as recited in claim 7, wherein said metal body comprises stainless steel.

14. An electrosurgical instrument as recited in claim 7, wherein said metal body has a thermal conductivity of at least about 0.35 W/cm° K. when measured at about 300° K.

15. An electrosurgical instrument as recited in claim 14, wherein said metal body comprises a first material selected from a group consisting of aluminum, silver, copper, gold, tungsten tantalum, columbium and molybdenum.

16. An electrosurgical instrument as recited in claim 7, wherein said metal body comprises:
a first metal layer defining said peripheral edge portion; and,
at least one second metal layer adjacent to said first metal layer, wherein said first metal layer and said at least one second metal layer comprise different materials.

17. An electrosurgical instrument as recited in claim 16, wherein the first metal layer comprises a first material selected from a group consisting of tungsten, tantalum, columbium and molybdenum.

18. An electrosurgical instrument as recited in claim 16, wherein said at least one second metal layer has a thermal conductivity of at least about 2 W/cm° K. when measured at about 300° K.

19. An electrosurgical instrument as recited in claim 18, wherein said at least one second metal layer comprises second material selected from a group consisting of gold aluminum, silver, and copper.

20. An electrosurgical instrument as recited in claim 1, wherein said sealing material comprises at least one of a group consisting of silicates, solutions containing silicates, and solutions forming silicates upon curing.

21. An electrosurgical instrument as recited in claim 20, wherein said sealing material penetrates at least about 10 percent of a total thickness of said insulating layer.

22. An electrosurgical instrument as recited in claim 1, wherein said sealing material has a kinematic viscosity of less than about 350 cSt.

23. An electrosurgical instrument as recited in claim 22, wherein said sealing material has a kinematic viscosity of less than about 200 cSt.

24. A method for manufacturing an electrosurgical instrument, comprising:
providing a substantially metallic element;
applying a porous insulating material over at least a portion of the substantially metallic element;
applying a sealing material over at least an outer surface of the insulating material, the sealing material being substantially hydrophobic and applied so as to penetrate at least a portion of the porous insulating material; and
curing the porous insulating material and sealing material to form a substantially sealed insulating layer.

25. The method as recited in claim 24, wherein said porous insulating material comprises a metal-oxide based binder.

26. The method as recited in claim 24, wherein said porous insulating material comprises at least one ceramic material.

27. The method as recited in claim 24, wherein said porous insulating material and sealing material are applied so the formed substantially sealed insulating layer has a thickness of less than 0.01 inches.

28. The method as recited in claim 24, wherein said sealing material is applied so as to penetrate at least about 10% of a total thickness of said porous insulating material.

29. The method as recited in claim 24, wherein said sealing material comprises at least one material from a group consisting of polydiorganosiloxanes and materials derived therefrom.

30. The method as recited in claim 24, wherein the substantially metallic element comprises a metal body having a main body portion and a peripheral edge portion.

31. The method as recited in claim 24, wherein the substantially metallic element comprises a metal body having a main body portion that is laterally-tapered down in cross-sectional to a peripheral edge portion.

32. The method as recited in claim 31, wherein the porous insulating material is applied so the peripheral edge portion is not covered by the substantially sealed insulating layer.

33. The method as recited in claim 32, wherein the insulating material and sealing material are applied so the formed substantially sealed insulating layer has a thickness of less than 0.01 inches.

34. The method as recited in claim 33, wherein the peripheral edge portion has a thickness less than about 1/10 of the maximum cross-sectional thickness of the main body portion.

35. The method as recited in claim 33, wherein the porous insulating material and sealing material are applied so as to form the substantially sealed insulating layer covering the entirety of said metal body apart from said peripheral edge portion.

36. The method as recited in claim 30, wherein said metal body is formed from stainless steel.

37. The method as recited in claim 30, wherein said metal body is formed from a metal that has a thermal conductivity of at least about 0.35 W/cm° K. when measured at about 300° K.

38. The method as recited in claim 30, wherein said metal body is formed from a first material selected from a group consisting of aluminum, silver, copper, gold, tungsten tantalum, columbium and molybdenum.

39. The method as recited in claim 30, wherein providing the substantially metallic body comprises:
forming a first metal layer defining said peripheral edge portion; and
roll-bonding at least one second metal layer onto said first metal layer, wherein said first metal layer and said at least one second metal layer comprise different materials.

40. The method as recited in claim 39, wherein the first metal layer comprises a first material selected from a group consisting of tungsten, tantalum, columbium and molybdenum.

41. The method as recited in claim 39, wherein said at least one second metal layer has a thermal conductivity of at least about 2 W/cm° K. when measured at about 300° K.

42. The method as recited in claim 41, wherein said at least one second metal layer comprises a second material selected from a group consisting of gold, aluminum, silver, and copper.

43. The method as recited in claim 42, wherein said sealing material comprises at least one of a group consisting of silicates, solutions containing silicates, and solutions forming silicates upon curing.

44. The method as recited in claim 42, wherein said sealing material is applied so the sealing material penetrates at least about 10 percent of a total thickness of the insulating material.

45. The method as recited in claim 24, wherein said sealing material has a kinematic viscosity of less than about 350 cSt.

46. The method as recited in claim 45, wherein said sealing material has a kinematic viscosity of less than about 200 cSt.

* * * * *